United States Patent [19]

Bara

[11] Patent Number: 5,919,468
[45] Date of Patent: Jul. 6, 1999

[54] PROCESS FOR THE COSMETIC TREATMENT OF THE SKIN COMPRISING APPLYING TO THE SKIN A SKIN CARE OR MAKE-UP COMPOSITION COMPRISING A SOLID ORGANOPOLYSILOXANE ELASTOMER ENCLOSED IN A FATTY PHASE

[75] Inventor: Isabelle Bara, Paris, France

[73] Assignee: L'Oreal, Paris, France

[21] Appl. No.: 08/802,082

[22] Filed: Feb. 19, 1997

[30] Foreign Application Priority Data

Feb. 19, 1996 [FR] France .................................. 96 02021

[51] Int. Cl.⁶ ................................ A61K 7/02; A61K 7/48
[52] U.S. Cl. ....................... 424/401; 424/78.03; 514/844; 514/937
[58] Field of Search ..................... 424/401, 489, 424/501, 78.03; 514/844, 845, 847, 937

[56] References Cited

U.S. PATENT DOCUMENTS 5,725,845    3/1998    Krog et al. ................................ 424/64

FOREIGN PATENT DOCUMENTS 0 293 795    12/1988    European Pat. Off. .
0 381 166     8/1990    European Pat. Off. .

OTHER PUBLICATIONS

English Derwent Abstract of JP 61194009.
English Derwent Abstract of JP 7258027.
English Derwent Abstract of JP 7258028.

*Primary Examiner*—Robert H. Harrison
*Attorney, Agent, or Firm*—Finnegan, Henderson, Farabow, Garrett & Dunner, L.L.P.

[57] ABSTRACT

The invention relates to the use of a partially crosslinked elastomeric solid organopolysiloxane in combination with a fatty phase for the preparation of a composition or in a composition for skin care or make-up for matting the skin, and to its various applications. The cosmetic compositions according to the invention are mild in application, easily spread, nonsticky and do not dry out the skin. They can be employed in particular for blurring out skin relief blemishes such as microreliefs, wrinkles or pores, while giving the skin a natural appearance.

16 Claims, No Drawings

PROCESS FOR THE COSMETIC TREATMENT OF THE SKIN COMPRISING APPLYING TO THE SKIN A SKIN CARE OR MAKE-UP COMPOSITION COMPRISING A SOLID ORGANOPOLYSILOXANE ELASTOMER ENCLOSED IN A FATTY PHASE

The present invention relates to the use of a partially crosslinked elastomeric solid organopolysiloxane in combination with a fatty phase for the preparation of a composition or in a composition for skin care or make-up for matting the skin, and to the various applications of this composition.

Skin care or make-up compositions which have matting properties are generally employed for solving shine problems caused by an excess of sebum and for improving the long-term behavior of the make-up, which tends to deteriorate visually in the course of the day. They give the skin a matte appearance resulting from a light-scattering ability at the surface of the skin. They can also be employed for blurring out skin blemishes such as microreliefs, wrinkles, lines, pores or color variations.

Conventional so-called matting compositions generally contain very little fatty substance or are devoid of fatty substance. They generally contain powders which adsorb the sebum and the excess oil of the composition which is not adsorbed by the skin. Matting powders of natural or synthetic origin include fillers such as talc, starch, mica, silica, nylon powders, polyethylene powders, poly-beta-alanine and poly(methyl methacrylate)s. Fillers of this type have the disadvantage of not imparting a natural appearance to the skin by giving a powdery or even plaster-like appearance and of accentuating skin blemishes. In addition, the compositions Also known, as described in European application EP-A-052 769, the disclosure of which is incorporated herein by reference, are matting compositions imparting a translucent layer and a natural appearance to skin which is made up. These compositions are dispersions of spherical particles in a fatty binder in a very specific fillers/binder weight ratio. These compositions can be desiccative; they have a tendency to pill when being spread and to impart a whitening effect to the skin because of a high concentration of powder.

Serums have also been proposed which are made from a water-soluble, more or less gelling phase that is devoid of a fatty phase and containing a low content of fatty substance. These formulations tend to be uncomfortable for the skin because of their low content of fatty substance and because of the presence of gelling agents, resulting in a sticky effect and a tensor effect on the skin.

The inventors have surprisingly discovered that the combination of a partially crosslinked elastomeric solid organopolysiloxane with a fatty phase constitutes a remarkable matting agent.

In fact, the inventors have discovered that such a combination makes it possible to obtain care or make-up compositions which have a good light-scattering ability at the surface, which are stable in time, and which give the skin a matte appearance for an extended time.

The inventors have also discovered that this combination makes it possible to obtain care or make-up products which enable the imperfections of the relief (surface) of the skin to be blurred out or deemphasized while giving it a natural appearance.

The partially crosslinked elastomeric organopolysiloxanes of the invention which are used in combination with, preferably enclosed in, a fatty phase have a remarkable ability to gel oil, are not desiccative for the skin and contribute good cosmetic properties. These new matting agents make it possible to formulate gels or creams which are comfortable to apply, mild, spread easily, nonsticky to the touch, and which do not dry out in the long term.

"Elastomeric" is intended to mean a deformable, flexible material which has viscoelastic properties and which exhibits, in particular, the consistency of a sponge or of a flexible sphere.

The partially crosslinked elastomeric organopolysiloxanes used in accordance with the invention are in general partially or completely crosslinked and of three-dimensional structure. When enclosed in a fatty phase, they are transformed, depending on the content of the fatty phase employed, from a product of spongy appearance when they are employed in the presence of a low content of fatty phase into a homogeneous gel in the presence of larger quantities of fatty phase. The gelling of the fatty phase by these elastomers may be complete or partial.

The matting agents of the invention are generally in the form of a gel containing a partially crosslinked elastomeric organopolysiloxane of three-dimensional structure, enclosed in at least one hydrocarbon oil and/or silicone oil.

The partially crosslinked elastomeric organopolysiloxanes according to the invention constituting the matting agent of the invention may be chosen from the crosslinked polymers described in European application EP-A-0295886, the disclosure of which is incorporated herein by reference.

According to that application, the crosslinked elastomeric organopoly- siloxanes are obtained by performing an addition and crosslink reaction, in the presence of a catalyst of the platinum type, of at least:

(a) an organopolysiloxane containing at least two lower alkenyl groups per molecule; and
(b) an organopolysiloxane containing at least two hydrogen atoms bonded to a silicon atom per molecule.

The partially crosslinked elastomeric organopolysiloxanes according to the invention constituting the matting agent may be chosen from those described in U.S. Pat. No. 5,266,321, the disclosure of which is incorporated herein by reference.

According to that patent, they are preferably chosen from:

(i) organopolysiloxanes containing $R_2SiO$ and $RSiO_{1.5}$ units and optionally $R_3SiO_{0.5}$ and/or $SiO_2$ units, in which the radicals R, $R_2$ and $R_3$, independently of one another, denote a hydrogen, an alkyl, such as methyl, ethyl or propyl, an aryl, such as phenyl or tolyl or an unsaturated aliphatic group, such as vinyl, and where the weight ratio of the $R_2SiO$ units to the $RSiO_{1.5}$ units varies from 1/1 to 30/1;

(ii) organopolysiloxanes which are insoluble and swellable in silicone oil, which are obtained by addition of an organohydropolysiloxane (1) and an organopolysiloxane containing unsaturated aliphatic groups (2), such that the quantity of hydrogen or of unsaturated aliphatic groups in (1) and (2) respectively ranges from 1 to 20 mol % when the organopolysiloxane is non-cyclic and from 1 to 50 mol % when the organopolysiloxane is cyclic.

The organopolysiloxanes forming a subject of the invention are, for example, those marketed under the names KSG6 by Shin-Etsu, TREFIL E-505C or TREFIL E-506C by Dow Corning, GRANSIL by Grant Industries (SR-CYC, SR DMF10, SR-DC556), or those marketed in the form of gels which are already formed (KSG15, KSG17, KSG16, KSG18 by Shin-Etsu, GRANSIL SR 5CYC gel, GRANSIL SR DMF 10 gel, GRANSIL SR DC 556 gel, SF 1204 and JK 113 from General Electric). A mixture of these commercial products may also be employed.

The fatty phase present in combination with, and preferably enclosing, the partially crosslinked elastomeric solid organopolysiloxane to form a matting agent comprises of at least one hydrocarbon oil and/or at least one silicone oil.

The hydrocarbon oils employed according to the invention which are present in combination with the partially crosslinked elastomeric organopolysiloxane are preferably chosen from:

- oils of animal origin, such as perhydrosqualene;
- vegetable oils such as liquid triglycerides, for example sunflower, corn, soya, marrow, grapeseed, sesame, hazelnut, apricot, macadamia, castor and avocado oils, or triglycerides of caprylic/capric acids, like those sold by Stearineries Dubois or those sold under the names MIGLYOL 810, 812 and 818 by Dynamit Nobel;
- the oils of formula $R_9COOR_{10}$ in which $R_9$ denotes the residue of a higher fatty acid containing from 7 to 19 carbon atoms and $R_{10}$ denotes a branched hydrocarbon chain containing from 3 to 20 carbon atoms, for example purcellin oil;
- linear or branched hydrocarbons of mineral or synthetic origin, such as paraffin oils and their derivatives, isoparaffin, isohexadecane, hydrogenated polyisobutene such as parleam and polydecenes;
- synthetic esters and ethers like isopropyl myristate and alcohol or polyalcohol octanoates, decanoates or ricinoleates;
- fatty alcohols like actyl dodecanol or oleyl alcohol; and mixtures thereof.

The silicone oils employed according to the invention which are present in combination with the partially crosslinked elastomeric organopolysiloxane are preferably chosen from linear polysiloxanes which are liquid or pasty at ambient temperature, such as methylpolysiloxane, methylphenylpolysiloxane, ethylpolysiloxane, ethylmethylpolysiloxane, ethylphenylpolysiloxane, hydroxymethylpolysiloxane, alkylpolydimethylsiloxane and cyclic polysiloxanes such as octamethylcyclopentasiloxane, decamethylcyclopentasiloxane, or mixtures thereof.

The organopolysiloxane is preferably present in the organopolysiloxane/fatty phase mixture in order to form the matting agent in the form of a more or less homogeneous gel in a concentration ranging from 1 to 80% by weight.

The resulting gel can be employed as it is and can itself constitute a care or make-up composition for matting the skin and/or for blurring out the blemishes of the relief of the skin. It can also be incorporated in a care or make-up formulation in a quantity which is sufficient to enable this composition to impart a good matting effect to the skin and/or to blur out satisfactorily the blemishes and/or color variations in the relief of the skin.

The compositions according to the invention containing the matting agents as defined above are preferably in the form of gels which may be translucent or opaque. They may also be in the form of oil/water emulsions or of water/oil emulsions in order to produce matting creams.

They may additionally contain conventional adjuvants such as water-soluble or liposoluble dyes, pigments, perfumes, preservatives, sunscreens and liposoluble or water-soluble agents. These adjuvants are present in quantities preferably ranging from 0 to 20% by weight relative to the weight of the composition.

They may additionally contain fillers in order to modify the texture of the formulation, such as silica, nylon powder, polyethylene powder, poly(methyl methacrylate) powder or its derivatives. These fillers are preferably present in quantities which range from 0 to 40% by weight relative to the weight of the composition.

Obviously, the adjuvants and the fillers introduced into the composition must be of a kind and in a quantity that are not detrimental to the effect which is sought after.

As indicated above, the matting effect of the composition according to the invention is linked with the scattering of light by the elastomeric organopolysiloxane. By virtue of this considerable scattering of light, the microrelief of the substrate onto which the composition is applied is no longer clearly visible. This effect is proportionally more remarkable as the composition is transparent. In particular, the transparency of the composition makes it possible to reduce the "projected shadows" of lines and wrinkles, and shadows which normally accentuate the relief of lines and wrinkles. Thus, the transparency of the composition offers an advantage not only in the visual effect of the composition but also, after application, in the effect obtained on the substrate.

Consequently, another subject of the invention comprises the use of a partially crosslinked elastomeric organopolysiloxane as defined above, in combination with, preferably enclosed in, a fatty phase for the preparation of a composition or in a composition for skin care or for make-up, in order to blur out the blemishes of the relief of the skin. In particular, in order to conceal the microreliefs., the wrinkles, the lines, and the pores.

The invention also relates to a process for nontherapeutic treatment of the skin, intended to give it a matte appearance and/or to conceal the blemishes of the relief of the skin, characterized in that a composition containing at least one partially crosslinked elastomeric organopolysiloxane as defined above is applied to the skin in an effective amount in the presence of a fatty phase.

The examples which follow serve to illustrate the invention without, however, being of a limiting nature.

| | |
|---|---|
| Polydimethylsiloxane oil 6 cst | 30% by weight |
| Partially crosslinked polydimethylorganosiloxane sold under the name KSG 6 by Shin Etsu | 20% by weight |
| Triglycerides of caprylic/capric acids, sold under the names MIGLYOL by Dynamit Nobel | 9.1% by weight |
| Parleam oil | 9.1% by weight |
| Silica sold under the name SB150 by Maprecos | 31.8% by weight |

A translucent, mild, easily spreadable gel which does not dry out was obtained merely by mixing and homogenizing the various ingredients at ambient temperature. The gel obtained possessed matting properties which were stable over time and gave a natural appearance once applied to the skin.

The change in the shine of the skin was measured in the course of time after 15 minutes, 2 hours, 4 hours, and 6 hours, as observed on a sample of 4 people (2 men and 2 women), each with a greasy and shiny skin, to whom the matting composition of Example 1 was applied.

The matting composition was applied to each person, at a rate of 2 mg/cm$^2$ in a single application to a half of the forehead, the other half serving as control region. A randomization was performed to avoid the region effects.

The climatic conditions were as follows:

- temperature: 21° C.
- relative moisture: 38%

The shine of the surface of the skin which is made up (or untreated in the case of the control region) was measured at times T=0 ($T_0$), T=15 min, T=2h, T =4h and T=6h, by means of a measuring instrument described in published French application FR 2,665,959, the disclosure of which is incorporated herein by reference, and starting with the parameters of parallel reflection and of cross- reflection which are specific to this device and which make it possible to evaluate the shine of the skin surface.

In the first step, at time T, the variation in the average shine measured on the treated region was calculated using the formula:

$$\Delta_1 = S'_T - S'_0 / S'_0$$

where: $S_0$ denotes the average shine measured at $T_0$, and $S_T$ denotes the average shine measured at T.

In the second step, at time T, the change in the average shine measured on the control region was calculated using the formula:

$$\Delta_2 = S'_T - S'_0 / S'_0$$

where: $S'_0$ denotes the average shine measured on the control region at $T_0$, and $S'_T$ denotes the average shine measured on the control region at T.

In the final step, the percentage change in the average shine was determined using the difference $\Delta_1 - \Delta_2$. This parameter allows the matting effect of the composition according to the invention to be determined, namely the percentage decrease in the shine and the behavior of the maftness in the course of time.

The results of these tests are summarized in the following table:

| Time | 15 minutes | 2 hours | 4 hours | 6 hours |
|---|---|---|---|---|
| Change in the average shine on treated region $\Delta_1$ | -18% | -12% | -10% | -9% |
| Change in the average shine on control region $\Delta_2$ | 10% | 11% | 18% | 12% |
| Percentage change in the average shine $\Delta_1 - \Delta_2$ | -28% | -23% | -28% | -21% |

According to the table, it has indeed been found that the composition of the invention matted very clearly after 15 min (28% decrease in the shine) and had a good behavior of the maftness in the course of time up to 6 hours (21% decrease in shine).

| | | |
|---|---|---|
| Mixture of 40% by weight of polydimethylsiloxane oil, 6 cst and of 60% by weight of partially cross-linked polydimethylorganosiloxane sold underthe name KSG 6 by Kose | 10% | by weight |
| Alkyl dimethicone copolyol surfactant sold under the name WE 09 by Goldschmidt | 5% | by weight |
| Perhydrosqualene | 10% | by weight |
| Preservative | q.s. | |
| Water | q.s. 100% | by weight |

A gelled, mild, easily spreadable cream which did not dry out was obtained merely by mixing and homogenizing the various ingredients at ambient temperature. The cream obtained had matting properties which were stable with time and gave a natural appearance once applied to the skin.

What is claimed is:

1. A method for matting the skin comprising the step of applying to said skin an effective amount of a skin care or make-up composition comprising an effective amount of at least one elastomeric solid organopolysiloxane enclosed in a fatty phase, wherein said at least one elastomeric solid organopolysiloxane is at least partially crosslinked.

2. A method according to claim 1, wherein said at least one elastomeric solid organopolysiloxane is completely crosslinked.

3. A method according to claim 1, wherein said fatty phase comprises at least one hydrocarbon oil or silicone oil.

4. A method according to claim 1, wherein said at least one elastomeric solid organopolysiloxane is obtained by performing an addition and crosslinking reaction of at least:

(a) an organopolysiloxane containing at least two lower alkenyl groups per molecule; and (b) an organopolysiloxane containing at least two hydrogen atoms bonded to a silicon atom per molecule, wherein said addition and crosslinking reactions occur in the presence of a catalyst.

5. A method according to claim 1, wherein said at least one elastomeric solid organopolysiloxane is selected from:

i) organopolysiloxanes containing $R_2SiO$ and $RSiO_{1.5}$ units, wherein R and $R_2$ denote, independently of one another, a hydrogen, an alkyl, an aryl, or an unsaturated aliphatic group, and wherein the weight ratio of $R_2SiO$ units to $RSiO_{1.5}$ units ranges from 1/1 to 30/1; and ii) organopolysiloxanes which are insoluble and swellable in silicone oil and which are obtained by addition of an organohydropolysiloxane and an organopolysiloxane containing unsaturated aliphatic groups, wherein the quantity of hydrogen or of unsaturated aliphatic groups in said organohydropolysiloxane and said organohydropolysiloxane ranges from 1 to 20 mol % when the organopolysiloxane is noncyclic and from 1 to 50 mol % when the organopolysiloxane is cyclic.

6. A method according to claim 5, wherein said organopolysiloxanes containing $R_2SiO$ and $RSiO_{1.5}$ units further contain units selected from $R_3SiO_{0.5}$ units, $SiO_2$ units, and mixtures thereof, wherein $R_3$ denotes a hydrogen, an alkyl, an aryl, or an unsaturated aliphatic group.

7. A method according to claim 3, wherein said at least one hydrocarbon oil is:

- an oil of animal origin;
    - a vegetable oil;
    - an oil of formula $R_9COOR_{10}$ in which $R_9$ denotes the residue of a higher fatty acid containing from 7 to 19 carbon atoms and $R_{10}$ denotes a branched hydrocarbon chain containing from 3 to 20 carbon atoms;
    - a linear or branched hydrocarbon of mineral or synthetic origin;
    - a synthetic ester or ether; or
    - a mixture thereof.

8. A method according to claim 7, wherein said oil of formula $R_9COOR_{10}$ is purcellin oil.

9. A method according to claim 3, wherein said at least one silicone oil is a linear polysiloxane which is liquid or pasty at ambient temperature, a cyclic polysiloxane or a mixture of said linear and cyclic polysiloxanes.

10. A method according to claim 1, wherein said at least one elastomeric solid organopolysiloxane is present in an amount effective to form a homogeneous gel.

11. A method according to claim 10, wherein said at least one elastomeric solid organopolysiloxane is present in an amount ranging from 1 to 80% by weight.

12. A method according to claim 1, wherein said skin care or make-up composition is in the form of a gel or cream.

13. A method according to claim 1, wherein said application step comprises blurring out blemishes of the skin.

14. A method according to claim 1, wherein said application step comprises concealing microreliefs and/or color variations of the skin.

15. A method according to claim 1, wherein said application step comprises concealing wrinkles and lines.

16. A method according to claim 1, wherein said application step comprises concealing pores of the skin.

* * * * *